United States Patent
Polig et al.

(10) Patent No.: US 11,150,926 B2
(45) Date of Patent: Oct. 19, 2021

(54) NATIVE CODE GENERATION FOR CLOUD SERVICES

(71) Applicant: International Business Machines Corporation, Armonk, NY (US)

(72) Inventors: Raphael Polig, Langnau am Albis (CH); Mitra Purandare, Zurich (CH); Matteo Manica, Zurich (CH); Roland Mathis, Zurich (CH)

(73) Assignee: International Business Machines Corporation, Armonk, NY (US)

( * ) Notice: Subject to any disclaimer, the term of this patent is extended or adjusted under 35 U.S.C. 154(b) by 230 days.

(21) Appl. No.: 16/282,459

(22) Filed: Feb. 22, 2019

(65) Prior Publication Data

US 2020/0272487 A1    Aug. 27, 2020

(51) Int. Cl.
*G06F 9/455* (2018.01)
*G06F 8/35* (2018.01)
*G06F 8/41* (2018.01)
*G06F 8/53* (2018.01)
*G06F 8/10* (2018.01)
(Continued)

(52) U.S. Cl.
CPC .............. *G06F 9/4552* (2013.01); *G06F 8/10* (2013.01); *G06F 8/35* (2013.01); *G06F 8/41* (2013.01); *G06F 8/53* (2013.01); *G06F 9/45558* (2013.01); *G06F 9/5072* (2013.01); *G06N 3/12* (2013.01); *H04L 63/0428* (2013.01); *H04L 67/10* (2013.01); *G06F 2009/45562* (2013.01)

(58) Field of Classification Search
None
See application file for complete search history.

(56) References Cited

U.S. PATENT DOCUMENTS

| | | | |
|---|---|---|---|
| 8,510,728 B2 * | 8/2013 | Burckart | ............. G06F 9/44521 717/166 |
| 9,038,038 B1 | 5/2015 | Jai et al. | |

(Continued)

FOREIGN PATENT DOCUMENTS

| | | |
|---|---|---|
| CN | 103945348 A | 7/2014 |
| CN | 104573063 A | 4/2015 |

OTHER PUBLICATIONS

S. Nepal et al., "TruXy: Trusted Storage Cloud for Scientific Workflows," in IEEE Transactions on Cloud Computing, vol. 5, No. 3, pp. 428-442, Jul. 1-Sep. 2017, doi: 10.1109/TCC.2015.2489638. (Year: 2017).*

(Continued)

*Primary Examiner* — Andrew M. Lyons
(74) *Attorney, Agent, or Firm* — Harrington & Smith

(57) ABSTRACT

An example of an embodiment is directed to a computer-implemented method for providing a cloud service to execute a computing task of a model specification. The method includes receiving, by the cloud service, the model specification and input data for the model specification from a user. The method further includes generating, by the cloud service, native code from the model specification and executing, by the cloud service, the computing task by executing the native code as a native process with the input data. The method also includes providing, by the cloud service, results of the computing task to the user. Other embodiments further concern a related computing system and a related computer program product.

18 Claims, 8 Drawing Sheets

(51) Int. Cl.
  *H04L 29/06* (2006.01)
  *H04L 29/08* (2006.01)
  *G06F 9/50* (2006.01)
  *G06N 3/12* (2006.01)

(56) References Cited

U.S. PATENT DOCUMENTS

| | | | |
|---|---|---|---|
| 9,201,635 B2 | 12/2015 | Jennings et al. | |
| 9,239,713 B1* | 1/2016 | Lakshman | G06F 9/451 |
| 9,569,184 B2 | 2/2017 | Tejani et al. | |
| 9,703,965 B1* | 7/2017 | Robinson | H04L 63/0428 |
| 10,127,030 B1* | 11/2018 | Mortman | H04L 9/3236 |
| 10,530,887 B1* | 1/2020 | Mehr | H04L 67/2847 |
| 2002/0038401 A1* | 3/2002 | Zaidi | G06F 13/28 710/305 |
| 2011/0125743 A1* | 5/2011 | Immonen | G06F 16/29 707/737 |
| 2014/0068583 A1 | 3/2014 | Tejani et al. | |
| 2014/0109078 A1* | 4/2014 | Lang | G06F 21/57 717/172 |
| 2014/0366007 A1 | 12/2014 | Koltachev et al. | |
| 2015/0161383 A1 | 6/2015 | Chen et al. | |
| 2016/0070591 A1 | 3/2016 | Yasuda | |
| 2016/0378474 A1* | 12/2016 | Gschwind | G06F 9/30021 712/224 |
| 2017/0242835 A1 | 8/2017 | Wolfram et al. | |
| 2017/0250979 A1* | 8/2017 | Benson | H04L 63/08 |
| 2019/0065693 A1* | 2/2019 | Mathis | G16H 20/00 |
| 2019/0079740 A1* | 3/2019 | Sharma | G06F 16/9535 |
| 2019/0253523 A1* | 8/2019 | Raduchel | H04L 9/0637 |
| 2020/0153623 A1* | 5/2020 | Asanghanwa | H04L 67/10 |
| 2020/0371755 A1* | 11/2020 | Patni | G06F 8/41 |

OTHER PUBLICATIONS

O. Mazonka, N. G. Tsoutsos and M. Maniatakos, "Cryptoleq: A Heterogeneous Abstract Machine for Encrypted and Unencrypted Computation," in IEEE Transactions on Information Forensics and Security, vol. 11, No. 9, pp. 2123-2138, Sep. 2016, doi: 10.1109/TIFS.2016.2569062. (Year: 2016).*

Written Opinion of the International Searching Authority. International Publication No. PCT/IB2020/050412 dated Apr. 22, 2020.

Ben Niu and Gang Tan "RockJIT: Securing Just-in-Time Compilation Using Modular Control-Flow Integrity" retrieved Feb. 21, 2019.

Ali-Reza Adl-Tabatabai, Michal Cierniak, Guei-Yuan Lueh, Vishesh M. Parikh, James M. Stichnoth "Fast, Effective Code Generation in a Just-in-Time Java Compiler" retrieved Feb. 21, 2019.

* cited by examiner

NATIVE CODE GENERATION FOR CLOUD SERVICES

BACKGROUND

The present invention relates to a computer-implemented method for providing a cloud service to execute a computing task associated to a model specification.

The present invention further relates to a corresponding computing system and a corresponding computer program product.

Many software applications rely on model specifications that need to be executed, simulated, or analyzed. The model specifications are commonly written in human readable text files and are decoupled from the code of the software application that executes the model. State-of-the-art software loads a specification and compiles it into efficient data structures that it can use. These data structures are interpreted to execute the desired behavior of the model. Such an interpretation step of the data structures may be a roadblock to achieve high performance of such applications.

SUMMARY

According to a first aspect, the invention is embodied as a computer-implemented method for providing a cloud service to execute a computing task of a model specification. The method comprises receiving, by the cloud service, the model specification and input data for the model specification from a user. The method further comprises generating, by the cloud service, native code from the model specification and executing, by the cloud service, the computing task by executing the native code as a native process with the input data. A further step comprises providing, by the cloud service, results of the computing task to the user.

Another aspect of the invention relates to a computing system for providing a cloud service to execute a computing task. The computing system comprises one or more memories having program code and one or more processors, wherein the one or more processors, in response to retrieval and execution of the program code, cause the computer system to perform operations comprising: implement the cloud service; receive a model specification and input data associated to the model specification from a user; generate native code from the model specification; execute the computing task by executing the native code as a native process with the input data; and provide results or in other words result data of the computing task to the user.

According to yet another aspect a computer program product for providing a cloud service to execute a computing task is disclosed. The computer program product comprises a computer readable storage medium having program instructions embodied therewith, the program instructions executable by a computing system of the cloud service to cause the cloud service to perform a method comprising: receiving a model specification and input data associated to the model specification from a user, generating native code from the model specification, executing the computing task by executing the native code as a native process with the input data and providing results of the computing task to the user.

Embodiments of the invention will be described in more detail below, by way of illustrative and non-limiting examples, with reference to the accompanying drawings.

DETAILED DESCRIPTION

Figure 1:
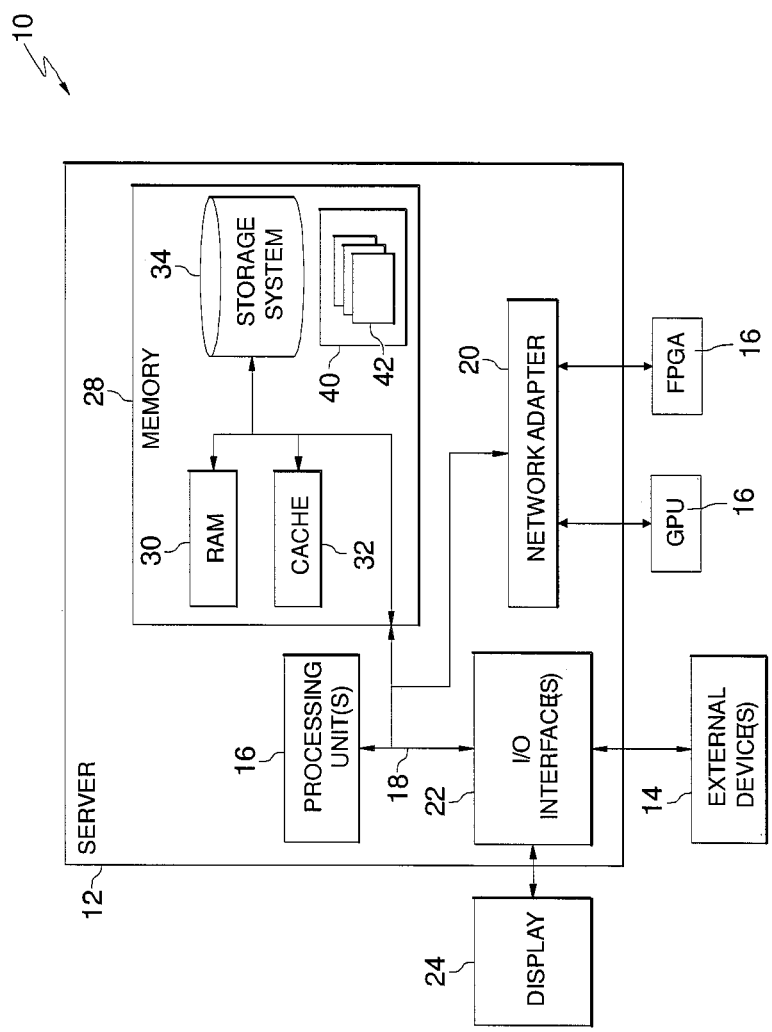
FIG. 1 depicts a cloud computing node according to an embodiment of the present invention.

In the context of this description, the following conventions, terms and/or expressions may be used:

Native code may be defined as programming code that is configured to run on a specific processor. The native code uses the specific instruction of the processor it was written for. Native code may generally not function if used on a processor or processing unit other than the one it was specifically written for. In order for the native code to run on a different processor than the one is was written for, the native code need to be run through an emulator program.

A container may be defined as a class, a data structure, or an abstract data type whose instances are collections of other objects. In other words, they store objects in an organized way that follows specific access rules. The size of the container depends on the number of objects it contains. Underlying implementations of various container types may vary in size and complexity.

Cloud services are often highly configurable by the end-user to suit his needs.

According to embodiments, a model specification may be generally defined as a specification of a computing task that shall be performed by a cloud service. As an example, a model/description of an electronic circuit may be provided as model description. Or for a deep learning service the model specification, training data and evaluation data may be supplied by the user. According to embodiments, the general structure of the model specification is generally known or at least known to the cloud service in order to facilitate the execution of computing tasks associated with the model specification. According to embodiments the model specification may be a gene regulatory network.

Embodiments disclose a computing system that converts a model specification into native code that implements the model behavior. This removes the overhead of the indirect execution of the model via data structures.

Furthermore, embodiments disclose a secure and safe execution environment for a model specification of a client to be executed in a cloud environment. The term secure shall refer in particular to the privacy of the client's model specification, input- and output data. The term safe shall mean in particular that a client's model specification which has been translated to native code can be executed in the cloud environment without compromising the stability or security of the provider application and systems.

It is to be understood that although this disclosure includes a detailed description on cloud computing, implementation of the teachings recited herein are not limited to a cloud computing environment. Rather, embodiments are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service. Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments described herein. Regardless, cloud computing node 10 is capable of being implemented and/or performing any of the functionality set forth herein.

In cloud computing node 10 there is a server 12, which is operational with numerous other general purpose or special purpose computing system environments or configurations. Examples of well-known computing systems, environments, and/or configurations that may be suitable for use with server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Server 12 may be described in the general context of computer system-executable instructions, such as program modules, being executed by a computer system. Generally, program modules may include routines, programs, objects, components, logic, data structures, and so on that perform particular tasks or implement particular abstract data types. Server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, server 12 in cloud computing node 10 is shown in the form of a general-purpose computing device. The components of server 12 may include, but are not limited to, one or more processors or processing units 16, a system memory 28, and a bus 18 that couples various system components including system memory 28 to processor 16. According to embodiments, server 12 may comprise several processing units 16, in particular a central processing unit (CPU), a graphics processing unit (GPU) and a field programmable gate array (FPGA).

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Server 12 typically includes a variety of computer system readable media. Such media may be any available media that is accessible by server 12, and it includes both volatile and non-volatile media, removable and non-removable media.

System memory 28 can include computer system readable media in the form of volatile memory, such as random access memory (RAM) 30 and/or cache memory 32. Server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments as described herein.

Server 12 may also communicate with one or more external devices 14 such as a keyboard, a pointing device, a display 24, etc.; one or more devices that enable a user to interact with server 12; and/or any devices (e.g., network card, modem, etc.) that enable server 12 to communicate with one or more other computing devices. Such communication can occur via Input/Output (I/O) interfaces 22. Still yet, server 12 can communicate with one or more networks such as a local area network (LAN), a general wide area network (WAN), and/or a public network (e.g., the Internet) via network adapter 20. According to embodiments, server 12 may communicate via the network adapter 20 with a graphics processing unit (GPU) 16 and/or a field programmable gate array (FPGA) 16.

As depicted, network adapter 20 communicates with the other components of server 12 via bus 18. It should be understood that although not shown, other hardware and/or software components could be used in conjunction with server 12. Examples, include, but are not limited to: microcode, device drivers, redundant processing units, external disk drive arrays, RAID systems, tape drives, and data archival storage systems, etc.

Figure 2:
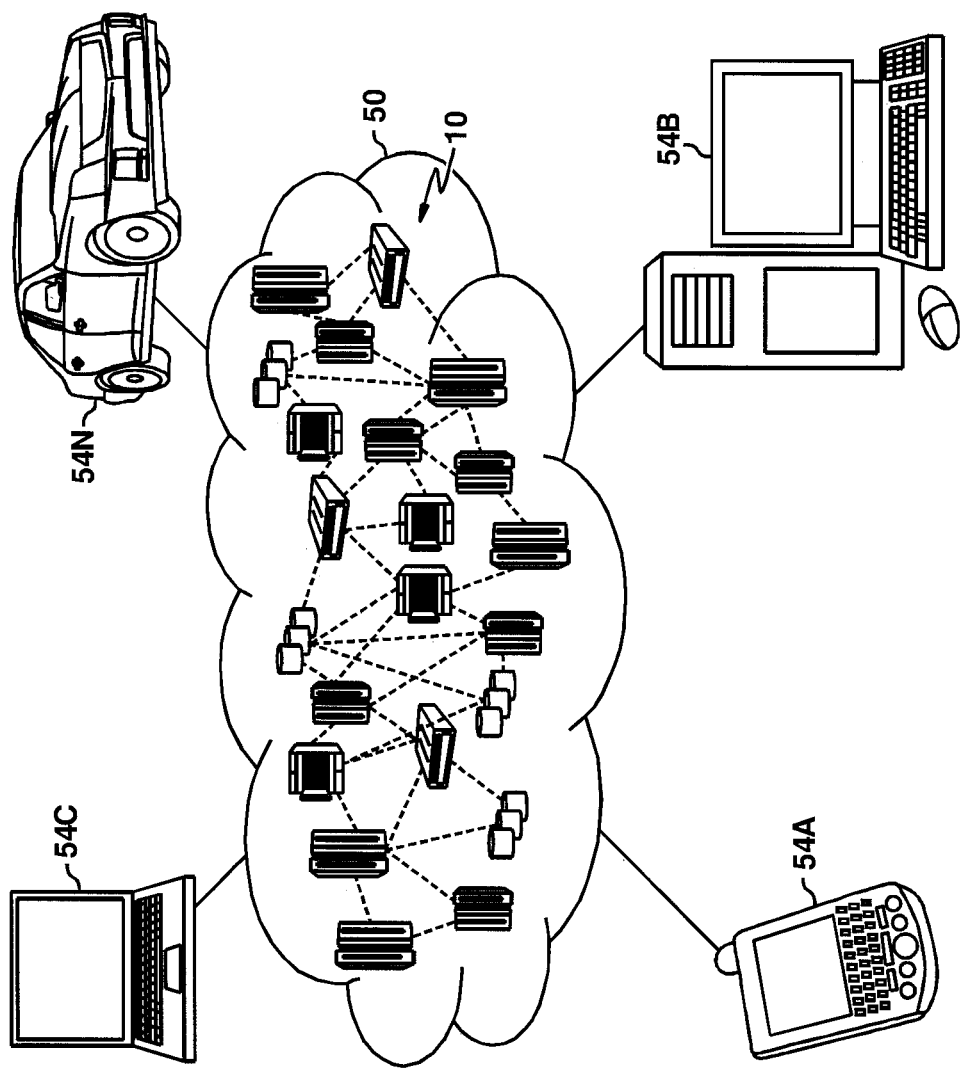
FIG. 2 depicts a cloud computing environment according to an embodiment of the present invention.

Referring now to FIG. 2, illustrative cloud computing environment 50 is depicted. As shown, cloud computing environment 50 includes one or more cloud computing nodes 10 with which local user devices used by cloud consumers, such as, for example, personal digital assistant (PDA) or cellular telephone 54A, desktop computer 54B, laptop computer 54C, and/or automobile computer system 54N may communicate. The user devices 54A, 54B, 54C and 54N may in the following be also generally referred to as user devices 54. The user devices 54 may belong to the same user or a user group. User devices 54 that belong to the same user or a user group are referred to as set 55 of user devices 54. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 3:
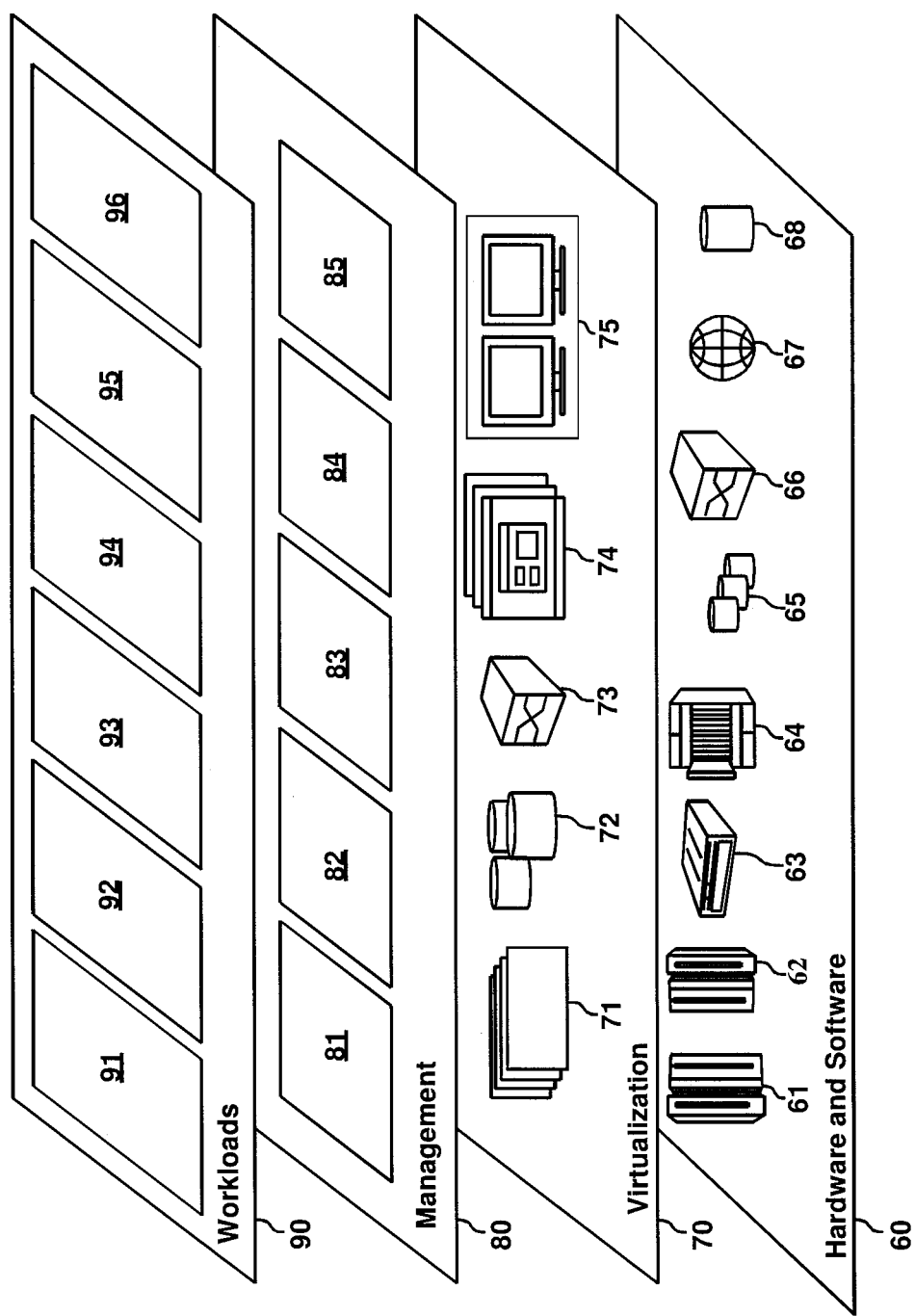
FIG. 3 depicts abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and providing anonymous storage services 96.

Figure 4:
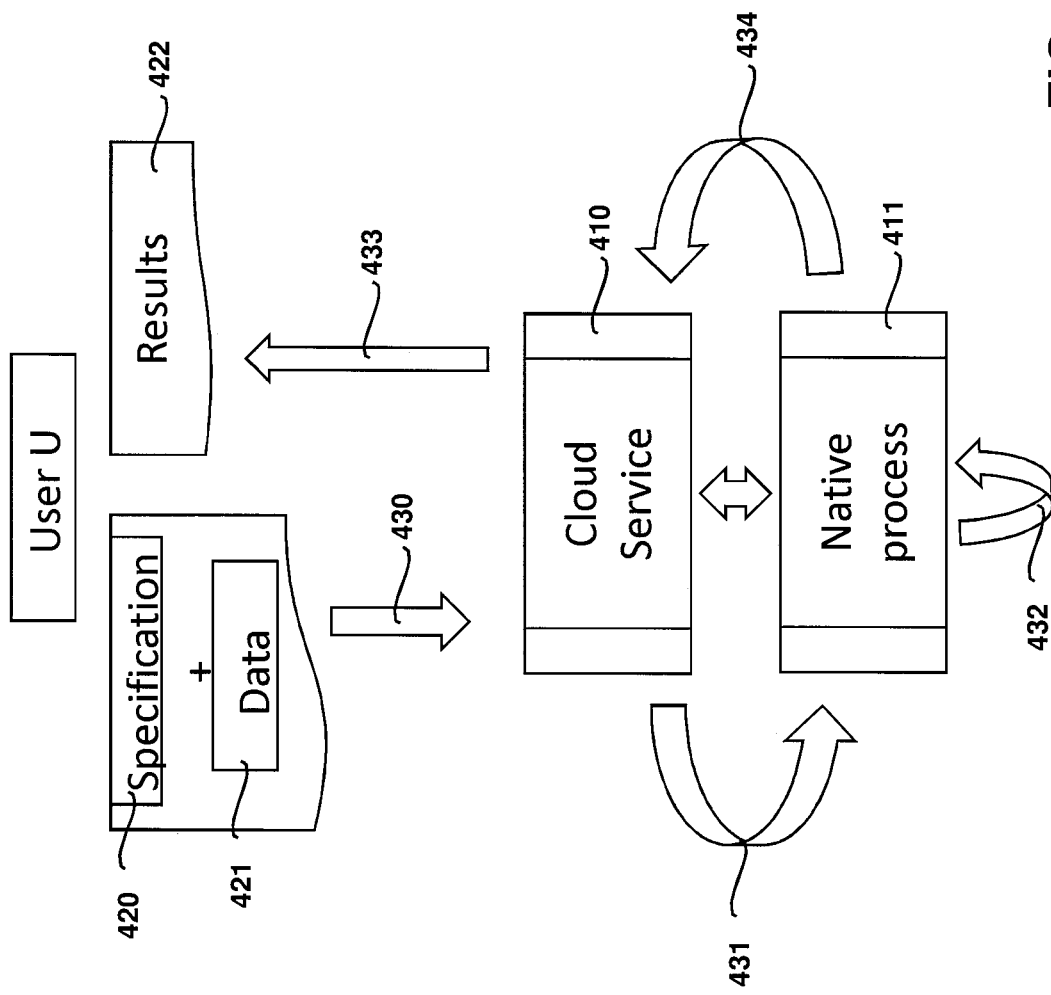
FIG. 4 shows a schematic flow diagram of a computer-implemented method for providing a cloud service according to an embodiment of the invention.

FIG. 4 shows a schematic flow diagram 400 of a computer-implemented method for providing a cloud service 410 according to an embodiment. The cloud service 410 is adapted to execute a computing task associated to a model specification 420.

At a step 430, the cloud service 410 receives the model specification 420 and input data 421 for the model specification 410 from a user U.

At a step 431, the cloud service 410 generates and compiles, e.g., just-in-time, a native code from the model specification 420 and starts a native process 411. This native code may be embedded with a (e.g., possibly pre-compiled) piece of code that has a predefined communication interface to the native code.

At a step 432, the cloud service 410 executes the computing task by executing the native code as native process 411 with the input data 421.

According to embodiments, the execution of the computing task may involve e.g. a simulation of the model specification 420. According to further embodiments, the execution of the computing task may additionally or alternately involve an analysis of the model specification 420.

Then, at a step 433, the cloud service 410 provides results 422 of the computing task to the user U. According to embodiments, the cloud service 410 may tear down the native process 411 at a step 434 after completion of the computing task to free up resources. This step 434 may include a tagging of the native code and storing the native code in a database/storage of the cloud service 410. Such a tagging and storage facilitates a reuse of the native code for future service requests of the same user. That is, the associated tag is generated so that the corresponding code can be easily retrieved from the database.

Spawning and tearing down the native processes can be done locally via commands of the operating system or remotely making use of a cloud management service such as OpenStack.

According to embodiments, the model specification 420 may be a Boolean network comprising a plurality of nodes and corresponding update function of the nodes. According to an embodiment, the model specification 420 may be a gene regulatory network and the input data 421 may be stimuli for the gene regulatory network. A gene (or genetic) regulatory network (GRN) may be defined as a collection of molecular regulators that interact with each other and with other substances in the cell to govern the gene expression levels of mRNA and proteins. The interaction can be direct or indirect. In other words, a "gene regulatory network" may be considered as a wiring diagram that represents how signaling pathways, transcription factors, and their target genes interact to orchestrate complex biological processes. Embodiments allow the simulation of large gene regulatory networks. The network topology is defined by the model specification provided by the user which comprises all update functions of all gene nodes in the network. Cloud services according to embodiments implement these functions as native code. This facilitates simulation performance which may be substantially higher compared with cloud services that operate at an interpreter level.

According to embodiments the user U may submit the gene regulatory network specification in JavaScript Object Notation (JSON) format defining a set of update functions for every node in the network.

The cloud service 410 receives this specification and translates it to a native representation in e.g. the C programming language for central processing units or in Verilog for field programmable gate arrays (FPGA)s.

This native representation is then compiled and linked with a predefined native application layer that provides means for the cloud service 410 to communicate with the user-specific part of the native application.

By using native code for executing the respective computing task, cloud services according to embodiments may benefit of up-to-date processor features. In other words, it allows taking full advantage of the features provided by the processor on which it is running. It may further enable the use of GPUs or FPGAs with user-specific tasks without jeopardizing the stability of the system.

Figure 5:
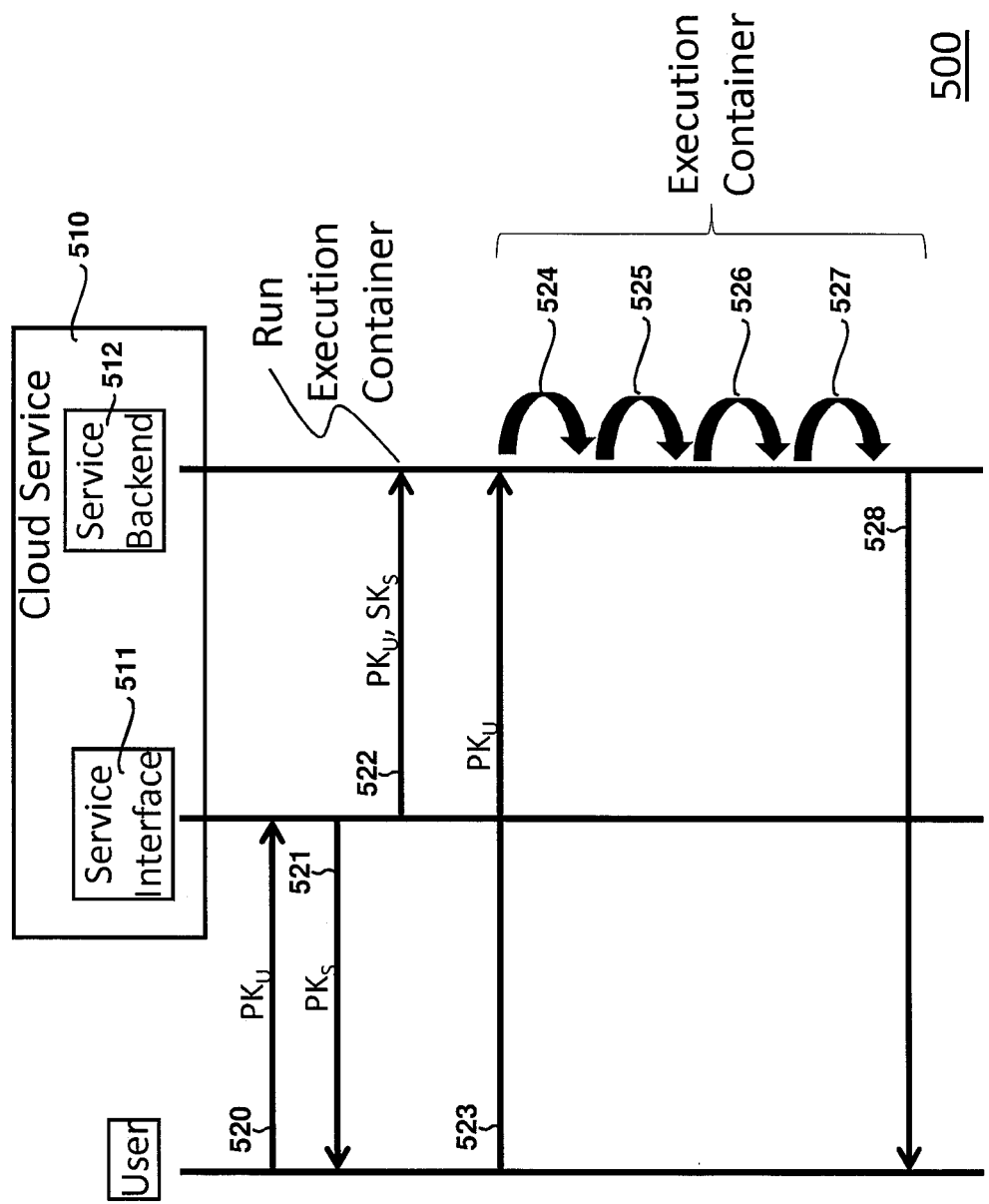
FIG. 5 shows a more detailed flow diagram of a computer-implemented method for providing a cloud service according to an embodiment of the invention.

FIG. 5 shows a more detailed flow diagram 500 of a computer-implemented method for providing a cloud service 510 according to an embodiment. The cloud service 510 comprises a service interface 511 to a user U and a service backend 512.

At a step 520, the cloud service 510, more particularly the service interface 511 of the cloud service 510, receives a service access request (SAR) from the user U. The service access request SAR comprises a user public key $PK_U$.

At a step 521, the service interface 511 provides a service public key $PK_S$ to the user U. The service public key $PK_S$ is a public key of the cloud service 510.

At a step 522, the cloud service 510 launches a user-specific execution container. The user-specific execution container is run by the service backend 512 and comprises the user public key $PK_U$ as well as a private service key $SK_S$ corresponding to the service public key $PK_S$. The user-specific execution containers are individual container instances that only belong to a single end-user.

The user U can now submit at steps 523 service execution requests comprising encrypted model specifications and encrypted input data to the service interface 521 being encrypted with the service public key. The service interface 511 will route the service execution requests to the user-specific execution container comprising the corresponding user public key.

The execution container may then decrypt, at a step 524, the encrypted model specification and the encrypted input data by means of the service secret key SKs corresponding to the service public key PKs.

The execution container may then, at a step 525, generate a native code from the decrypted model specification and execute, at a step 526, the computing task by executing the native code as native process with the decrypted input data. Finally, the execution container encrypts the results of the computing task, at a step 527, by means of the user public key $PK_U$.

Finally, the cloud service 510 provides, at a step 528, the encrypted results to the user U.

More particularly, the execution container sends the result to the service interface 511 which forwards it to the user U.

Hence in such an embodied system the user-specific execution containers are the only processes that are able to decrypt the encrypted model specifications and input data. Furthermore, all communications to and from the execution containers is encrypted and the model specification and input data of each user is running in a separate container when in clear-text.

According to embodiments, the application which executes the computing task is hosted as a Software as a Service (SaaS) on the cloud. By providing encrypted execution containers, the model specification as well as the input and output data can be secured from any unauthorized access during transmission and execution. This is of particular importance as the design of such model specifications may be a lengthy process and hence may establish an important asset of a client using the cloud service for the execution of the respective computing task.

Figure 6:
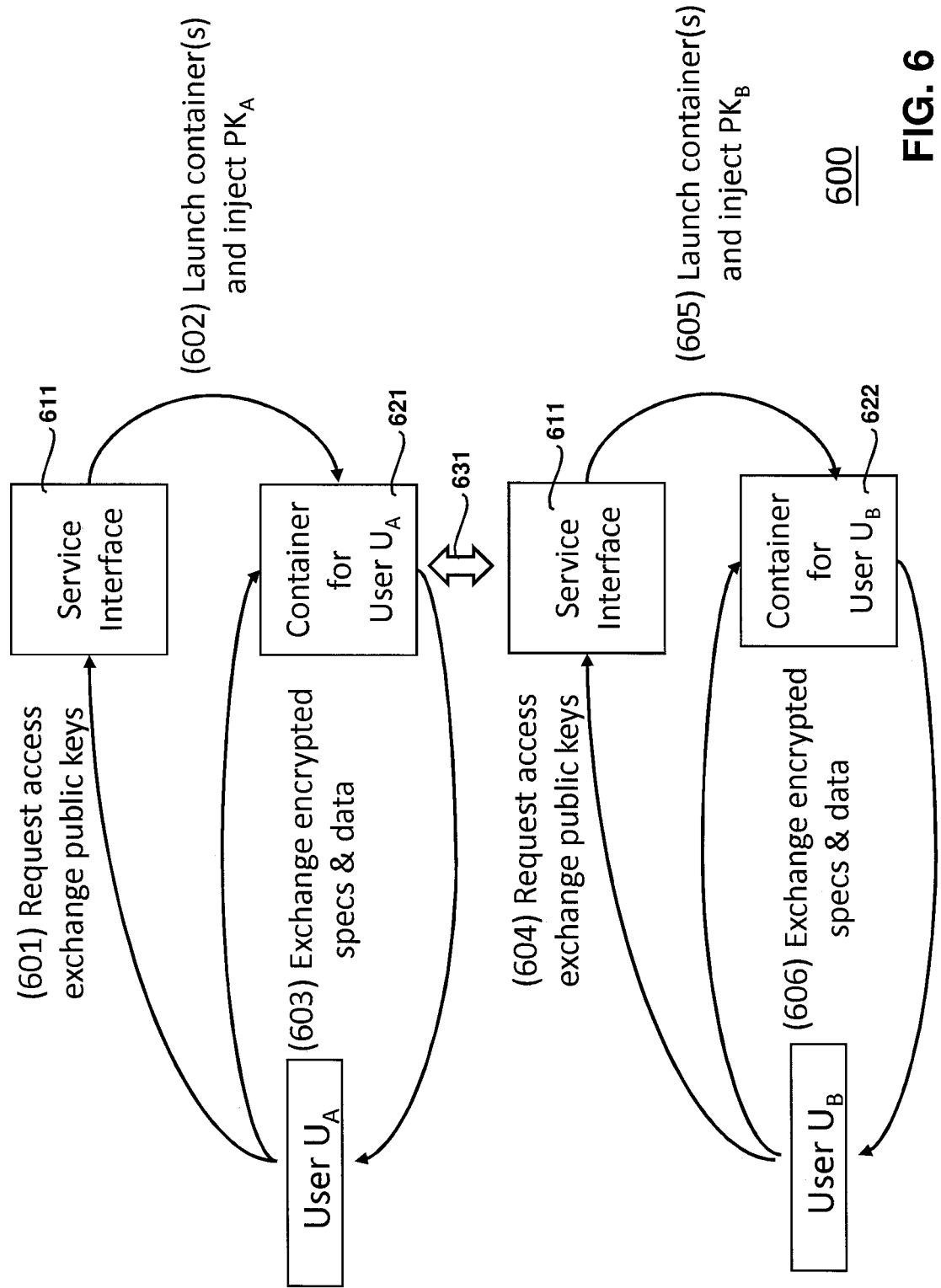
FIG. 6 shows another schematic flow diagram of a computer-implemented method for providing a cloud service according to an embodiment of the invention.

FIG. 6 shows another schematic flow diagram 600 of a computer-implemented method for providing a cloud service according to an embodiment. In particular, flow diagram 600 illustrates the use of container technology for providing a secure execution environment for two different user $U_A$ and $U_B$.

At a step 601, a first user $U_A$ sends a service access request to a service interface 611 of a cloud service. The first user $U_A$ exchanges public keys with the service interface 611. More particularly, it sends a user public key $PK_A$ and receives a service public key $PK_S$.

At a step 602, the service interface 611 initiates a launch of an execution container 621 for the first user $U_A$. This includes the injection of the user public key $PK_A$ into the container 621.

Then, at subsequent steps 603, the first user $U_A$ may exchange encrypted model specifications and associated data, in particular input data and result data, with the execution container 621, in a secure way.

In parallel (illustrated by reference 631), a second user $U_B$ may send at a step 604 a service access request to the service interface 611 of the cloud service. The registration performed during step 604 includes an exchange of public keys with the service interface 611. More particularly, the second user $U_B$ sends a user public key $PK_B$ to the service interface 611 and receives a service public key $PK_S$.

At a step 605, the service interface 611 initiates a launch of an execution container 622 for the second user $U_B$. This includes the injection of the user public key $PK_B$ into the container 622.

Then, at subsequent steps 606, the second user $U_B$ may exchange encrypted model specifications and associated data, in particular input data and result data, with the execution container 622, in a secure way.

It should be noted that according to embodiments multiple execution containers may be launched per user to satisfy performance needs.

Figure 7:
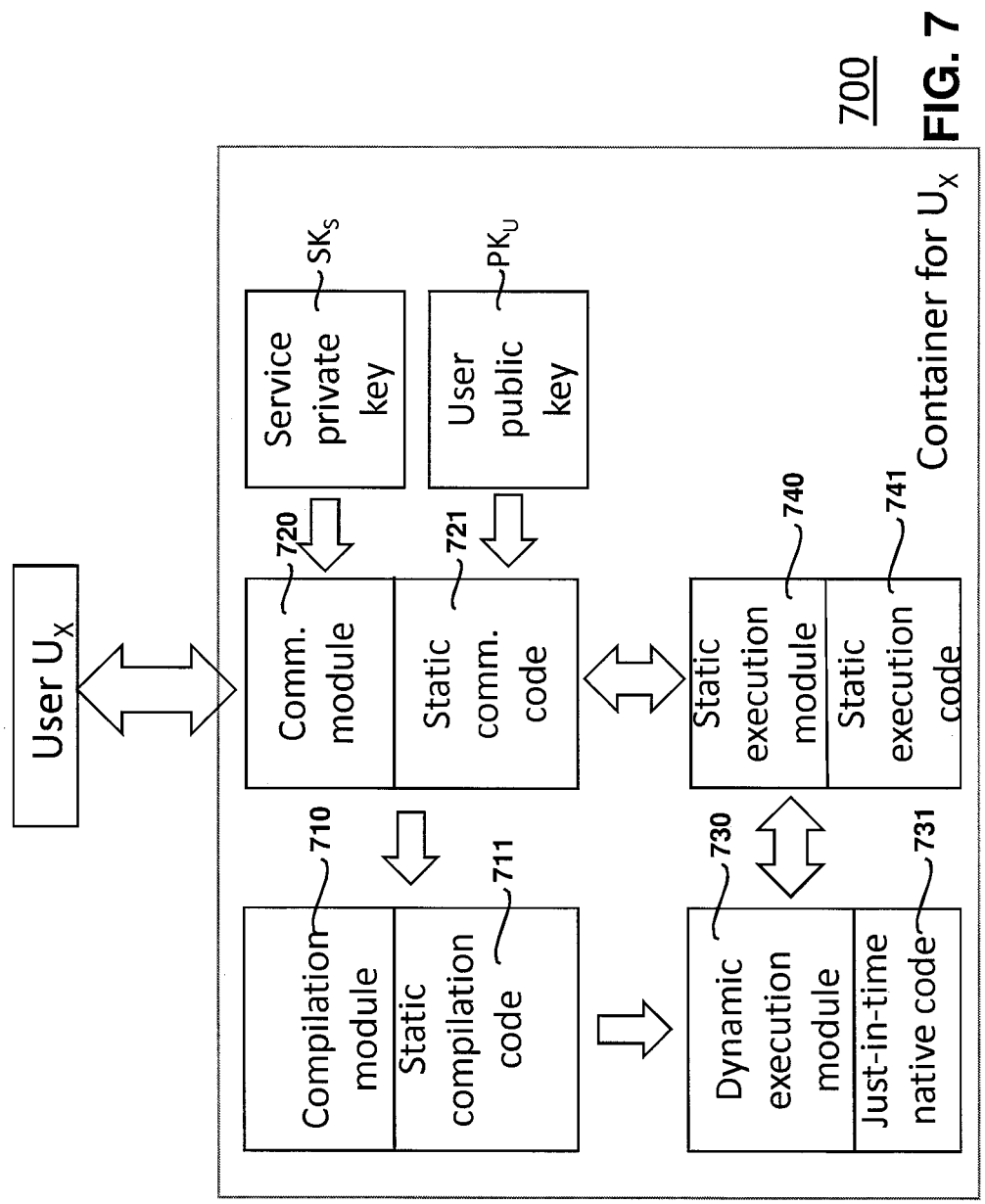
FIG. 7 illustrates functional modules of an execution container according to an embodiment of the invention.

FIG. 7 illustrates functional modules of an execution container 700 according to an embodiment. The execution container 700 comprises a compilation module 710 which is configured to compile native code from the model specification. The compilation module 710 may comprise in particular static compilation code 711 which may be used for all execution containers of the cloud service. That is, the static compilation code 711 may be the same for all the execution containers, hence this phrase uses the term "static".

The execution container 700 further comprises a communication (comm.) module 720 configured to communicate with a service interface of the cloud service, e.g. with the service interface 512 of FIG. 5. The communication module 720 may comprise in particular static communication code 721 which may be used for all execution containers of the cloud service. The communication module 720 comprises in particular code for communicating with a message queue system.

The execution container 700 further comprises a dynamic execution module 730 configured to execute the native code 731. The native code 731 is generated just-in-time from the received model specification and may hence be different for each execution container 700. The dynamic execution module 730, which may also be denoted as a native code module, is generated every time the user submits a new model specification to the cloud service.

The execution container 700 further comprises a static execution module 740 configured to execute static execution code 741. The static execution code may be used for all execution containers of the cloud service. That is, the static execution code 741 refers to the code of the static execution module 740, which is a master process controlling the execution of the dynamic execution module 730.

More specifically, the static execution module 740 may interact with the dynamic execution module 730 via inter process communication mechanisms and may start and terminate a dynamic execution module. The dynamic execution module 730 can be started as a separate process by the static execution module 740 and may contain a few additional static routines to allow communication.

In addition, the execution container 700 comprises a user public key $PK_U$ and a service private key SKs. According to embodiments, the native code that is generated by the compilation module 710 is native code that is specifically compiled for a central processing unit CPU of the respective cloud service, e.g. for the processing unit 16 of the server 10 as shown in FIG. 1. According to embodiments, the native code 711 that is generated by the compilation module 710 is native code that is specifically compiled for a graphics processing unit (GPU) of the respective cloud service. According to embodiments, the native code that is generated by the compilation module 710 is native code that is specifically compiled for a field programmable gate array (FPGA) of the respective cloud service.

According to embodiments, to protect against access from the cloud provider the application provider may use instruction extensions to protect the code of the model specification and the corresponding cleartext input/output data from being accessed. This may be achieved by declaring the model specification and the input and output data as sensitive data and allow only trusted code access to these memory locations. The model specification and data can enter and leave this area encrypted providing a higher level of security.

Figure 8:
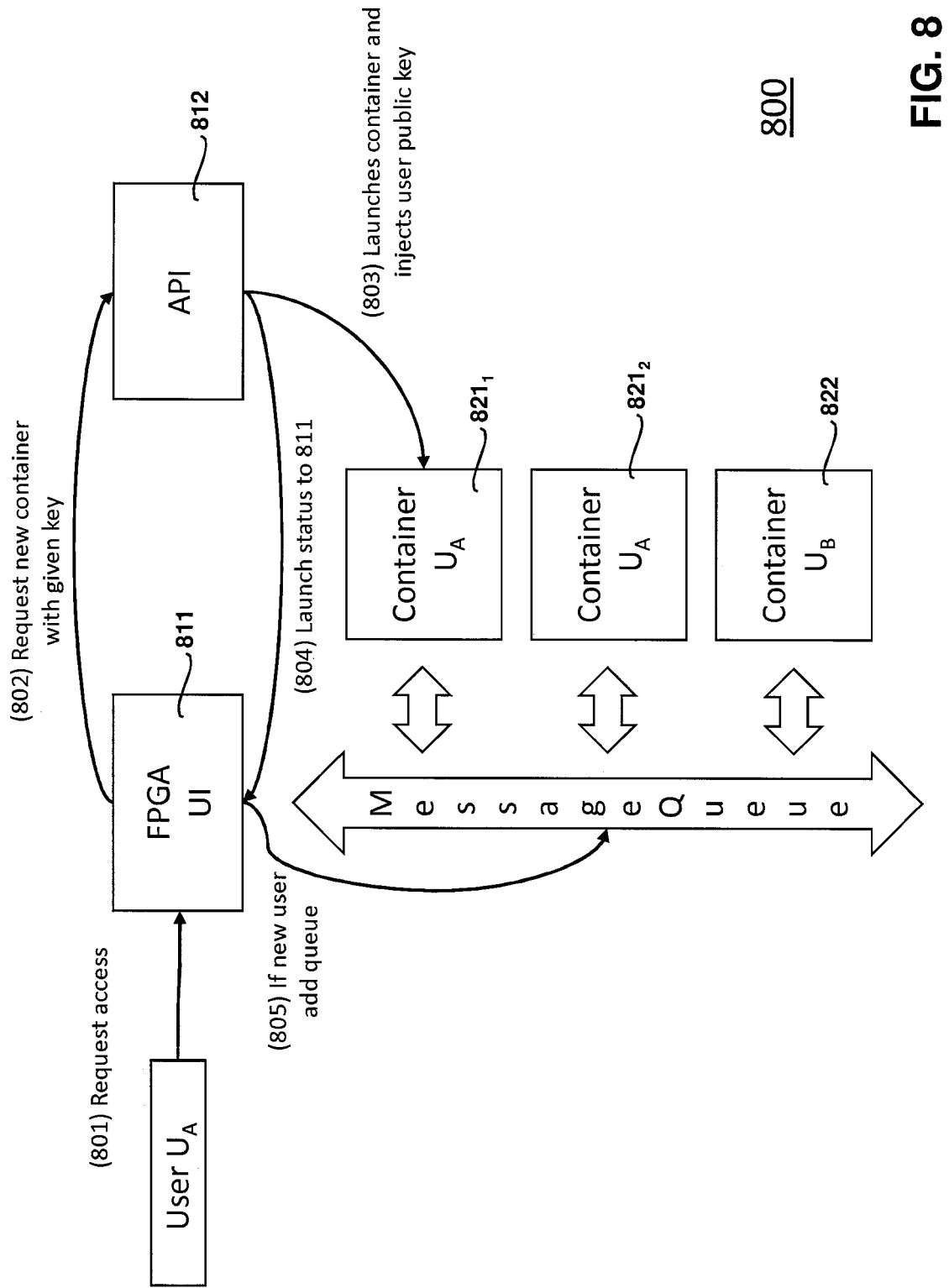
FIG. 8 shows another schematic flow diagram of a computer-implemented method for providing a cloud service according to an embodiment of the invention.

FIG. 8 shows another schematic flow diagram 800 of a computer-implemented method for providing a cloud service according to an embodiment.

At a step 801, a user $U_A$ sends a service access request to a service interface 811 of a cloud service. The service interface 811 may be e.g. a user interface of an FPGA. After exchanging the corresponding public keys (user public key $PK_A$ and service public key $PK_S$), the service interface 811 validates the user key, and in the case of a positive outcome, grants the user access. At a step 802, there is a request for a new container with the give key, and the issuance of a new execution container by an application programming interface (API) 812 of a cloud operating system. Such a cloud operating system may control a large pool of compute, storage and networking resources throughout a datacenter. The API 812 may be e.g. an API of the OpenStack operating system. The cloud operating system then launches, at a step 803, an execution container $821_1$ for the user $U_A$. In addition, the cloud operating system launches, at a step 804, the corresponding status to the service interface 811. The communication between the service interface 811 and the execution containers may be performed via message queuing (MQ). According to an embodiment, the message queuing system Rabbit MQ may be used. A new receive queue is created on the MQ system before an execution container is launched. When launching the execution container, it is configured to listen to this specific queue via a startup parameter. The outputs of all execution container instances are sent to the same queue which is read by the service logic and further processed, e.g. visualized and/or stored in database. Accordingly, if the user $U_A$ is a new user, the service interface 811 adds, at a step 805, a message queue. According to embodiments, multiple containers may be launched per user to satisfy performance needs. According to the example of FIG. 8, another execution container $821_2$ for the user $U_A$ is provided. Furthermore, FIG. 8 shows another execution container 822 for another user $U_B$.

The present invention may be a system, a method, and/or a computer program product. The computer program product may include a computer readable storage medium (or media) having computer readable program instructions thereon for causing a processor/processing unit, e.g. one or more of the processing units 16 of the server 12, to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage, device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for providing a cloud service to execute a computing task of a model specification, the method comprising
   providing by the cloud service user-specific execution containers for a plurality of users of the cloud service, wherein individual ones of the user-specific execution containers are to have an associated service secret key and a corresponding user public key to access the individual user-specific execution container;
   communicating by the cloud service with a user to receive a user public key from the user and to send a service public key to the user for use by the user for encryption and decryption of information;
   receiving, by the cloud service, a service access request from the user, the service access request comprising the user public key;
   launching, by the cloud service, a user-specific execution container for the user based on the received user public key and a service secret key corresponding to the service public key and the user public key;
   receiving, by the cloud service and from the user, the model specification and input data as stimuli for the model specification and encrypted at least by the user public key;
   running the user-specific execution container for the user, to perform at least:
      generating, by the cloud service, native code from the model specification;
      executing, by the cloud service, the computing task by executing the native code as a native process with the input data as stimuli; and
      providing, by the cloud service, results of the computing task to the user using at least the user public key.

2. A computer-implemented method according to claim 1, wherein the execution of the computing task comprises a simulation of the model specification, an analysis of the model specification, or both the simulation of the model specification and the analysis of the model specification.

3. A computer-implemented method according to claim 1, wherein the method comprises
   tearing down the native process after completion of the computing task;
   tagging the native code; and
   storing the native code in a database of the cloud service.

4. A computer-implemented method according to claim 1, wherein
   the model specification comprises a Boolean network comprising a plurality of nodes and update functions of the nodes.

5. A computer-implemented method according to claim 4, wherein
   the model specification comprises a gene regulatory network; and
   the input data comprises stimuli for the gene regulatory network.

6. A computer-implemented method according to claim 1, the method comprising
   performing the communicating by the cloud service with the plurality of users to transfer corresponding user public keys and service public keys for corresponding user-specific execution containers;
   launching, by the cloud service, the corresponding user-specific execution containers for the plurality of users based on received user public keys and service secret keys corresponding to the service public keys and the user public keys;
   running the user-specific execution containers for the plurality of users to perform at least:
      generating, by the user-specific execution containers, corresponding native code from corresponding model specifications;
      executing, by the user-specific execution containers, corresponding computing tasks by executing the corresponding native code as native processes with the corresponding input data; and
      encrypting all communications to and from the user-specific execution containers.

7. A computer-implemented method according to claim 1 wherein the execution containers are configured to perform the following:
   compile native code from the model specification;
   communicate with a service interface of the cloud service;
   execute the native code; and
   execute static execution code.

8. A computer-implemented method according to claim 7, wherein
   the compilation of the native code from the model specification, the communication with a service interface of the cloud service, and the execution of the static execution code, are performed by static code; and
   at least some of the plurality of execution containers of the cloud service comprise a same static code.

9. A computer-implemented method according to claim 1, wherein the native code is native code for a central processing unit.

10. A computer-implemented method according to claim 1, wherein the native code is native code for a general processing unit.

11. A computer-implemented method according to claim 1, wherein the native code is native code for a field programmable gate array.

12. The method of claim 1, wherein the model specification comprises a specification of the computing task and is to be executed, simulated, or analyzed via the computing task by the cloud service using the input data and wherein the native code uses specific instructions of one or more processors in the cloud service to implement the model specification.

13. A computer-implemented method for providing a cloud service to execute a computing task of a model specification, the method comprising
receiving, by the cloud service, the model specification and input data for the model specification from a user;
generating, by the cloud service, native code from the model specification;
executing, by the cloud service, the computing task by executing the native code as a native process with the input data; and
providing, by the cloud service, results of the computing task to the user,
receiving, by the cloud service, a service access request from a user, the service access request comprising a user public key;
providing, by the cloud service, a service public key of the cloud service to the user;
launching, by the cloud service, a user-specific execution container comprising the user public key;
receiving, by the cloud service, an encrypted model specification and encrypted input data from the user, the encrypted model specification and the encrypted input data being encrypted with the service public key;
routing, by the cloud service, the encrypted model specification and the encrypted input data to the user-specific execution container comprising the corresponding user public key;
decrypting, by the user-specific execution container, the encrypted model specification and the encrypted input data by means of a service secret key corresponding to the service public key;
generating, by the user-specific execution container, a native code from the decrypted model specification;
executing, by the user-specific execution container, the computing task by executing the native code as native process with the decrypted input data;
encrypting, by the user-specific execution container, results of the computing task by means of the user public key into encrypted results; and
providing, by the cloud service, the encrypted results of the computing task to the user.

14. A computing system for providing a cloud service to execute a computing task, the computing system comprising one or more memories having program code and one or more processors, wherein the one or more processors, in response to retrieval and execution of the program code, cause the computer system to perform operations comprising:
implement the cloud service;
provide by the cloud service user-specific execution containers for a plurality of users of the cloud service, wherein individual ones of the user-specific execution containers are to have an associated service secret key and a corresponding user public key to access the individual user-specific execution container;
communicate by the cloud service with a user to receive a user public key from the user and to send a service public key to the user for use by the user for encryption and decryption of information;
receive, by the cloud service, a service access request from the user, the service access request comprising the user public key;
launch, by the cloud service, a user-specific execution container for the user based on the received user public key and a service secret key corresponding to the service public key and the user public key;
receive, by the cloud service and from the user, a model specification and input data as stimuli for the model specification and encrypted at least by the user public key;
running the user-specific execution container for the user, to perform at least:
generate, by the cloud service, native code from the model specification;
execute, by the cloud service, the computing task by executing the native code as a native process with the input data as stimuli;
provide, by the cloud service, results of the computing task to the user using at least the user public key.

15. A computing system according to claim 14, wherein the one or more processors, in response to retrieval and execution of the program code, cause the computer system to perform operations comprising:
tear down the native process after completion of the computing task;
tag the native code; and
store the native code in a database of the cloud service.

16. A computing system according to claim 14, wherein the one or more processors, in response to retrieval and execution of the program code, cause the computer system to perform operations comprising:
perform the communicating by the cloud service with the plurality of users to transfer corresponding user public keys and service public keys for corresponding user-specific execution containers;
launch, by the cloud service, the corresponding user-specific execution containers for the plurality of users based on received user public keys and service secret keys corresponding to the service public keys and the user public keys;
run the user-specific execution containers for the plurality of users to perform at least:
generate, by the user-specific execution containers, corresponding native code from corresponding model specifications;
execute, by the user-specific execution containers, corresponding computing tasks by executing the corresponding native code as native processes with the corresponding input data; and
encrypt all communications to and from the user-specific execution containers.

17. A computing system according to claim 14, wherein the one or more processors, in response to retrieval and execution of the program code, cause the computer system to perform operations comprising:
wherein the execution containers are configured to perform the following:
compile native code from the model specification;
communicate with a service interface of the cloud service;
execute the native code; and
execute static execution code.

18. A computer program product for providing a cloud service to execute a computing task, the computer program product comprising a computer readable storage medium having program instructions embodied therewith, the program instructions executable by a computing system of the cloud service to cause the cloud service to perform a method comprising:
providing by the cloud service user-specific execution containers for a plurality of users of the cloud service, wherein individual ones of the user-specific execution containers are to have an associated service secret key and a corresponding user public key to access the individual user-specific execution container;

communicating by the cloud service with a user to receive a user public key from the user and to send a service public key to the user for use by the user for encryption and decryption of information;

receiving, by the cloud service, a service access request from the user, the service access request comprising the user public key;

launching, by the cloud service, a user-specific execution container for the user based on the received user public key and a service secret key corresponding to the service public key and the user public key;

receiving, by the cloud service and from the user, a model specification and input data as stimuli for the model specification and encrypted at least by the user public key;

running the user-specific execution container for the user, to perform at least:
  generating native code from the model specification;
  executing the computing task by executing the native code as a native process with the input data as stimuli; and
  providing results of the computing task to the user using at least the user public key.

* * * * *